(12) United States Patent
Griesbach et al.

(10) Patent No.: US 6,615,836 B1
(45) Date of Patent: Sep. 9, 2003

(54) SURGICAL DRAPE HAVING A POCKET-FORMING FEATURE

(75) Inventors: Henry L. Griesbach, Clarkston, GA (US); Greg S. Hafer, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/723,311

(22) Filed: Nov. 27, 2000

(51) Int. Cl.$^7$ .............................................. A61B 19/00
(52) U.S. Cl. ....................................... 128/849; 128/852
(58) Field of Search ................................. 128/849–856

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,802,817 A | 4/1974 | Matuski et al. |
| 3,849,241 A | 11/1974 | Buntin et al. |
| 3,855,046 A | 12/1974 | Hansen et al. |
| 3,881,474 A | 5/1975 | Krzewinski |
| 3,962,618 A | 6/1976 | Burton et al. |
| 4,041,203 A | 8/1977 | Brock et al. |
| 4,323,062 A | 4/1982 | Canty |
| 4,340,563 A | 7/1982 | Appel et al. |
| 4,379,192 A | 4/1983 | Wahlquist et al. |
| 4,957,120 A | 9/1990 | Grier-Idris |
| 5,010,899 A | 4/1991 | Thompson |
| 5,339,831 A | 8/1994 | Thompson |
| 5,345,946 A | 9/1994 | Butterworth et al. |
| 5,388,593 A | 2/1995 | Thomalla |
| 5,418,045 A | 5/1995 | Pike et al. |
| 5,494,050 A | 2/1996 | Reyes |
| 5,495,935 A | 3/1996 | Zabron et al. |
| 5,540,979 A | 7/1996 | Yahiaoui et al. |
| 5,647,376 A | 7/1997 | Thompson |
| 5,669,900 A | 9/1997 | Bullwinkel et al. |
| 5,858,515 A | 1/1999 | Stokes et al. |
| 5,906,269 A | 5/1999 | Zabron et al. |
| 5,962,117 A | 10/1999 | Furutani et al. |
| 5,964,742 A | 10/1999 | McCormack et al. |
| 5,997,981 A | 12/1999 | McCormack et al. |
| 6,055,987 A | 5/2000 | Griesbach et al. |
| 6,216,700 B1 | 4/2001 | Griesbach et al. |
| 6,314,959 B1 | 11/2001 | Griesbach et al. |

FOREIGN PATENT DOCUMENTS

| | | |
|---|---|---|
| EP | 0374730 A3 | 12/1989 |
| EP | 0374730 A2 | 6/1990 |
| GB | 2285408 A | 7/1995 |
| WO | WO 9933408 | 7/1999 |

OTHER PUBLICATIONS

PCT Search Report for Appl. No. PCT/US98/27645; Mar. 25, 1999.
PCT Search Report for Int'l Application No. PCT/US01/44400, Jul. 10, 2002.

Primary Examiner—Michael A. Brown
(74) Attorney, Agent, or Firm—Dority & Manning, P.A.

(57) ABSTRACT

A surgical drape is provided that is capable of forming a pocket. In particular, the surgical drape includes a fabric formed from a nonwoven layer. The nonwoven layer has a surface that includes a plurality of strands arranged on the surface with a plurality of bonds spaced about the surface. The nonwoven layer also includes a plurality of loops extending between the bonds. The surgical drape also includes at least one hook fastener that contains hooks engageable with the loops of the nonwoven layer. As a result, an edge of the fabric can be folded such that the hooks engage the loops of the fabric to form a pocket. The pocket can have one open end, two open ends, or two closed ends.

29 Claims, 11 Drawing Sheets

SURGICAL DRAPE HAVING A POCKET-FORMING FEATURE

BACKGROUND OF THE INVENTION

Various types of surgical drapes have been used to keep a surgical site on a patient sterile during a surgical procedure. Traditionally, surgical drapes were linen or woven cloth, and were sterilized after each use for reuse. More recently, disposable drapes have been introduced, in which a nonwoven paper or fabric forms a substantial part of the drape. A reinforcement area is often placed around a fenestration or an edge of disposable surgical drapes to provide structural strength and to absorb bodily fluids from a surgical site. Many disposable drapes also include a number of layers of different materials for the drape area and reinforcement area, with each layer providing a different property to the drape. For example, spunbond fabrics, meltblown fabrics, and polymer films have been used as layers in disposable drapes.

Many different shapes of surgical drapes have been proposed, often depending upon the specific surgical procedure to be performed. For example, the shape of the drape is often specifically designed to fit around a specific surgical site on the body. In some cases, a fenestration, as mentioned above, is provided through a drape to allow medical personnel access to the surgical site, whereas the remaining sheet portion of the drape covers the rest of the body and table. Moreover, several drapes are often used in combination to cover a patient. In some cases, several rectangular drapes, often called universal drapes, are laid over the patient in a pattern providing an opening through which the medical personnel can access the surgical site while also covering the remainder of the patient's body and the table.

Nevertheless, one problem with such conventional drapes is that various objects and tools cannot be easily stored on top of the drapes without falling off or without becoming contaminated. In response, some drapes have been developed to maintain medical devices during a surgical procedure. For instance, U.S. Pat. No. 5,010,899 describes a surgical drape including a plurality of binding strips of material attached to the upper surface of the drape for maintaining medical devices during a surgical procedure. The strips may include a fastening system that uses VEL-CRO® hook fasteners and an engageable loop material or an adhesive strip for sealing the strip over onto itself. However, the strips are limited to a single placement on the drape and thus do not provide flexibility or adjustability, especially in view of the demands of newer surgical procedures and tools.

As such, a need currently exists for a surgical drape that better allows the storage or placement of certain medical tools, instruments, cords, etc., thereon without falling off or becoming contaminated.

SUMMARY OF THE INVENTION

In accordance with one embodiment of the present invention, a method of forming a surgical drape with a pocket is provided. The method includes providing a fabric including a nonwoven layer. The nonwoven layer has a surface that includes a plurality of strands (e.g., fibers, filaments, etc.) that are arranged on the surface with a plurality of bonds spaced about the surface. The nonwoven layer also includes a plurality of loops extending between the bonds.

The method also includes forming a pocket by folding an edge of the fabric in a certain direction such that the edge engages a portion of the fabric. For example, pockets having two open ends, one open end, or two closed ends can be formed utilizing a variety of folding techniques. In one embodiment, a pocket having two closed ends can be formed by double-folding an edge of the fabric and then tucking under the ends of the fold.

In addition, the method also includes securing the edge of the fabric to a portion of the fabric using at least one hook-fastener that includes a plurality of hooks that are engageable with said loops. In some embodiments, the hook fastener(s) can be formed integral with the fabric. Moreover, in other embodiments, the hook fastener(s) can be formed separate from the fabric.

In accordance with another embodiment of the present invention, a method for forming a surgical drape with a pocket is provided. The method includes providing a fabric having a surface that defines a loop-element region and a hook-element region. The loop-element region is defined by a surface of a nonwoven layer that includes a plurality of strands. The strands are arranged on the surface of the nonwoven layer with a plurality of bonds spaced about the surface of the nonwoven layer and a plurality of loops extending between the bonds. In addition, the hook-element region has at least one hook fastener integrally disposed thereon, which includes a plurality of hooks.

The method also includes forming a pocket by folding an edge of the fabric in a certain direction such that the edge engages a portion of the fabric. For example, pockets having two open ends, one open end, or two closed ends can be formed utilizing a variety of folding techniques. In one embodiment, a pocket having two closed ends can be formed by double-folding an edge of the fabric and then tucking under the ends of the fold. Further, the method includes securing the edge of the fabric to a portion of the fabric using at least one hook-fastener that includes a plurality of hooks that are engageable with the loops.

In accordance with still another embodiment of the present invention, a surgical drape is provided that includes a fabric having a surface defining a loop-element region and a hook-element region. The loop-element region is defined by a surface of a nonwoven layer that includes a plurality of strands. The strands are arranged on the surface of the nonwoven layer with a plurality of bonds spaced about the surface of the nonwoven layer and a plurality of loops extending between the bonds. In addition, the hook-element region has at least one hook fastener integrally disposed thereon, which includes a plurality of hooks. One edge of the fabric is foldable such that the hooks can engage the loop to form a pocket. The pocket can have two open ends, one open end, or two closed ends.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Repeated use of reference characters in the present specification and drawings is intended to represent the same or analogous features or elements of the invention.

DETAILED DESCRIPTION OF REPRESENTATIVE EMBODIMENTS

As used herein, the terms "nonwoven web" or "nonwoven" refers to a web having a structure of individual fibers or threads which are interlaid, but not in an identifiable manner as in a knitted fabric. Nonwoven webs or fabrics have been formed from many processes, such as, for example, meltblowing processes, spunbonding processes, and bonded carded web processes. The basis weight of nonwoven fabrics is usually expressed in ounces of material per square yard (osy) or grams per square meter (gsm) and the fibers diameters are usually expressed in microns. (Note that to convert from osy to gsm, multiply osy by 33.91).

As used herein, the term "fiber" generally refers to an elongated strand of defined length, such as staple fibers formed by cutting a continuous strand into lengths of, for example, 2 to 5 cm. Collections of fibers may have the same or different lengths.

As used herein, the term "filament" refers to a generally continuous strand that has a large ratio of length to diameter, such as, for example, a ratio of 1000 or more.

As used herein, "meltblown fibers" refers to fibers formed by extruding a molten thermoplastic material through a plurality of fine, usually circular, die capillaries as molten threads or filaments into converging high velocity, usually hot gas (e.g., air) streams which attenuate the filaments of thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin etal.

As used herein, "spunbond fibers" refer to small diameter fibers that are formed by extruding molten thermoplastic material as filaments from a plurality of fine, usually circular capillaries of a spinneret with the diameter of the extruded fibers, and then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. No. 3,338,992 to Kinney, U.S. Pat. No. 3,341,394 to Kinney, U.S. Pat. No. 3,502,763 to Hartman, and U.S. Pat. No. 3,542,615 to Dobo et al. Spunbond fibers are generally not tacky when they are deposited on a collecting surface.

As used herein, the phrase "thermal point bonding" generally refers to passing a fabric (e.g., fibrous web or multiple fibrous web layers) to be bonded between a heated calendar roll and an anvil roll. The calendar roll is usually patterned in some way so that the entire fabric is not bonded across its entire surface, and the anvil roll is usually smooth. As a result, various patterns for calendar rolls have been developed for functional as well as aesthetic reasons. One example of a pattern has points and is the Hansen-Pennings or "H&P" pattern with about a 30% bond area with about 200 pins/square inch as taught in U.S. Pat. No. 3,855,046. The H&P pattern has square point or pin bonding areas. Another typical point bonding pattern is the expanded Hansen-Pennings or "EHP" bond pattern which produces a 15% bond area. Another typical point bonding pattern designated "714" has square pin bonding areas wherein the resulting pattern has a bonded area of about 15%. Other common patterns include a diamond pattern with repeating and slightly offset diamonds with about a 16% bond area and a wire weave pattern looking as the name suggests, e.g., like a window screen, with about an 18% bond area. Typically, the percent bonding area varies from around 10% to around 30% of the area of the fabric. As is well known in the art, the bonding holds the fabric together.

As used herein, the phrases "pattern unbonded", "point unbonded", or "PUB" generally refer to a fabric pattern having continuous thermally bonded areas defining a plurality of discrete unbonded areas. The fibers or filaments within the discrete unbonded areas are dimensionally stabilized by the continuous bonded areas that encircle or surround each unbonded area, such that no support or backing layer of film or adhesive is required. The unbonded areas are specifically designed to afford spaces between fibers or filaments within the unbonded areas. A suitable process for forming the pattern-unbonded nonwoven material, such as described in U.S. Pat. No. 5,962,117, which is incorporated herein in its entirety by reference thereto for all purposes, includes providing a nonwoven fabric (e.g., nonwoven web or multiple nonwoven web layers), providing oppposedly positioned first and second calendar rolls and defining a nip therebetween, with at least one of the rolls being heated and having a bonding pattern on its outermost surface comprising a continuous pattern of land areas defining a plurality of discrete openings, apertures, or holes, and passing the nonwoven fabric or web within the nip formed by the rolls. Each of the openings in the roll or rolls defined by the continuous land areas forms a discrete unbonded area in at least one surface of the nonwoven fabric in which the fibers or filaments of the fabric are substantially or completely unbonded. Stated alternatively, the continuous pattern of land areas in the roll or rolls forms a continuous pattern of bonded areas that define a plurality of discrete unbonded areas on at least one surface of the nonwoven fabric. An alternative embodiment of the process includes pre-bonding the nonwoven fabric before passing the fabric within the nip formed by the calender rolls.

It should be noted that any given range presented herein is intended to include any and all lesser included ranges. For example, a range of from 45–90 would also include 50–90; 45–80; 46–89 and the like. Thus, the range of 95% to 99.999% also includes, for example, the ranges of 96% to 99.1%, 96.3% to 99.7%, and 99.91 to 99.999%.

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

In general, the present invention is directed to a surgical drape that is capable of forming a pocket. For example, in one embodiment, a surgical drape of the present invention contains a fabric that includes an edge capable of being folded in one or more directions to form a pocket having two open ends, one open end, and/or two closed ends. In some embodiments, the edge of the fabric can be secured using a hook fastener that is integrally formed into the fabric. In other embodiments, the edge of the fabric can be secured using a hook fastener that is formed separately from the fabric but that can releasably attach thereto. It has been discovered that the pockets of drapes formed according to the present invention are adjustable and can possess multiple configurations to hold tools or other objects of various sizes or shapes and/or to allow fluids to be transferred away from the surgical site.

Surgical drapes formed in accordance with the present invention can generally possess any of a variety of sizes and shapes, depending on the particular use of the drape and on its desired properties. For example, certain surgical drape configurations are described in U.S. Pat. No. 6,055,987 to Griesbach. et al., which is incorporated herein in its entirety by reference thereto for all purposes.

Figure 1:
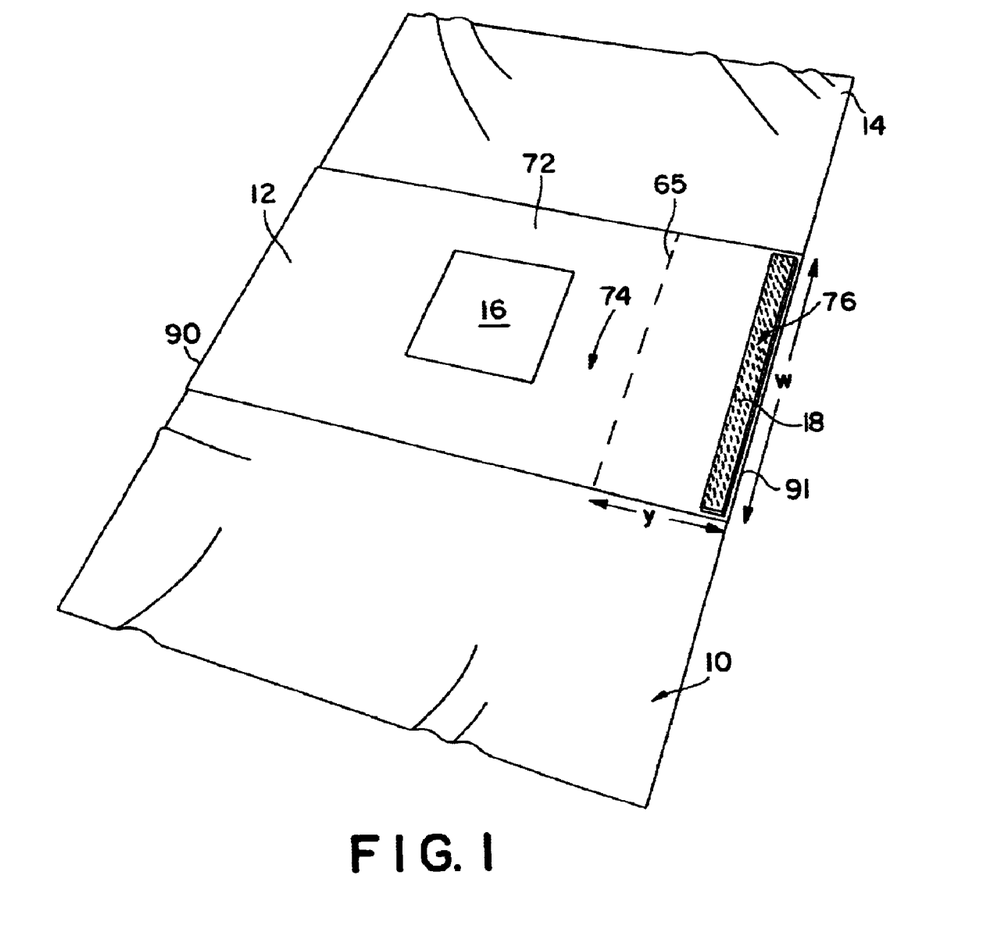
FIG. 1 is a perspective view of one embodiment of a surgical drape of the present invention.
Figure 2:
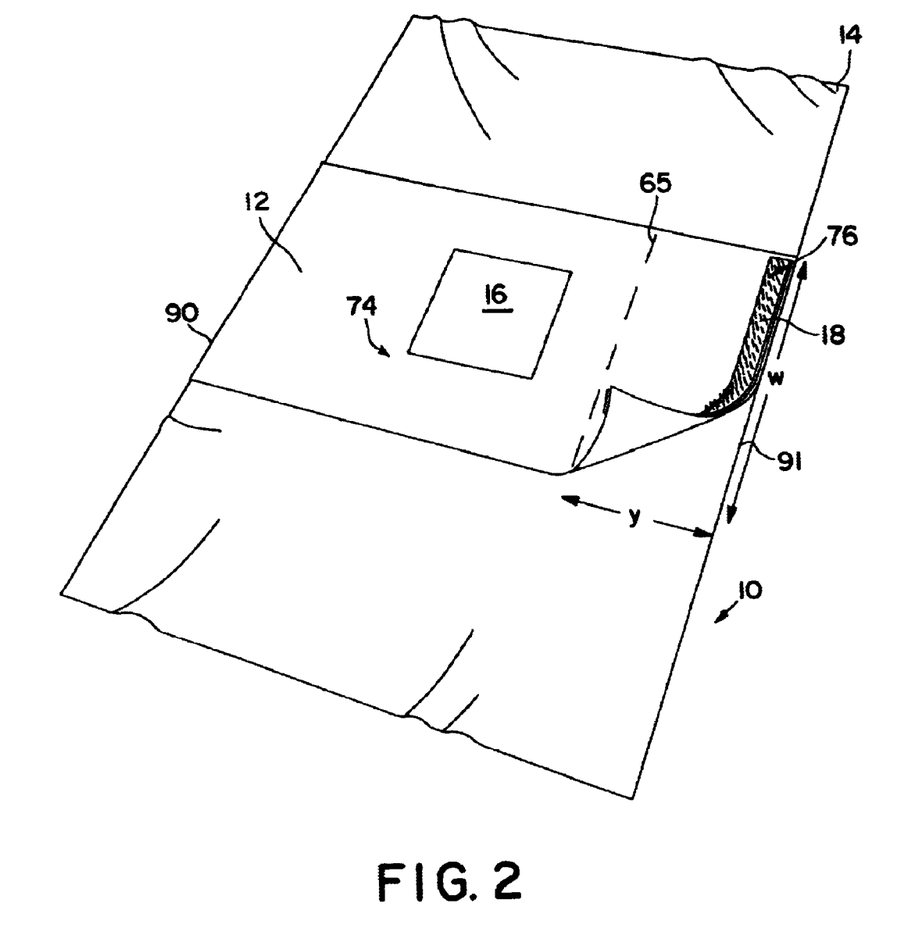
FIG. 2 is an illustration of the surgical drape of FIG. 1 with one unattached end of the surface fabric lifted back from the base sheet.
Figure 3:
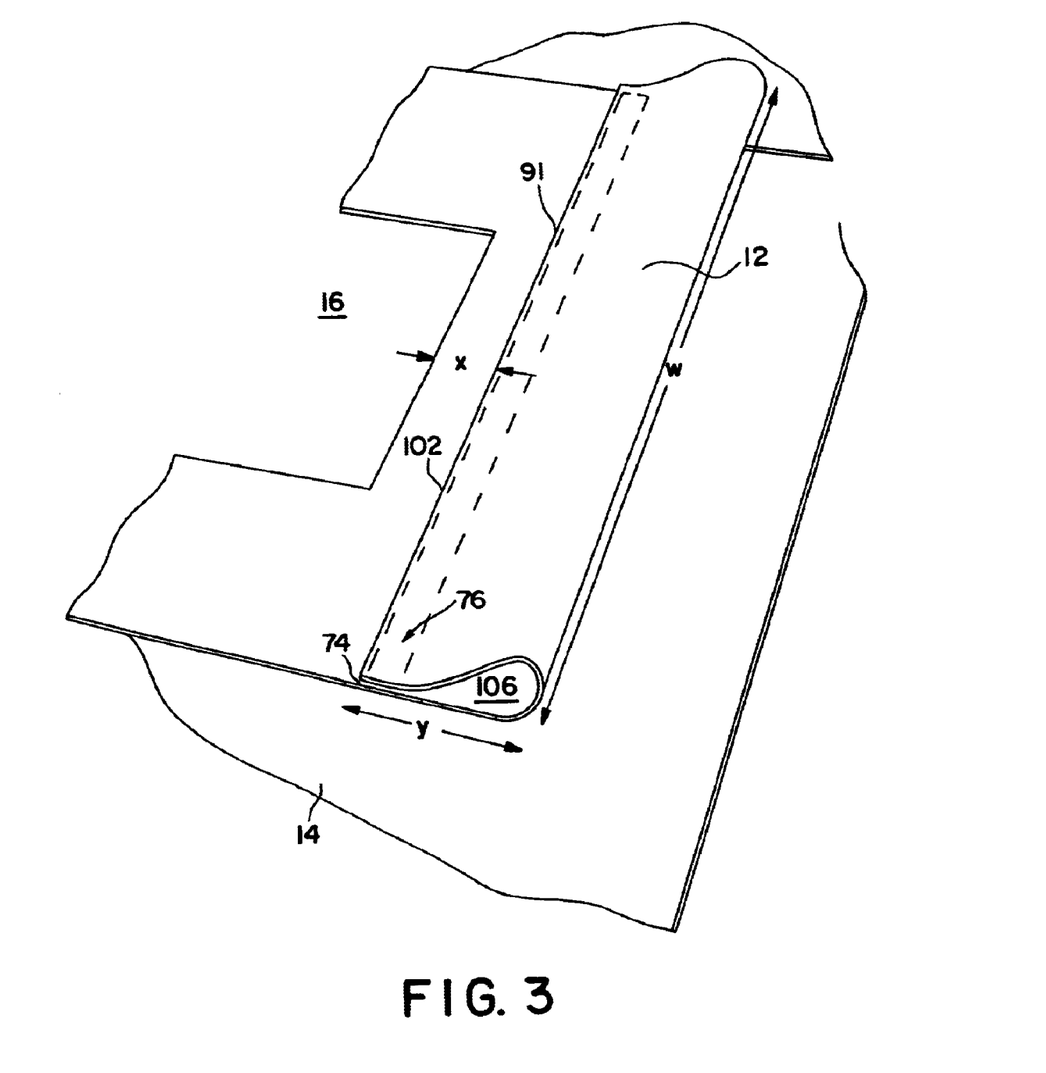
FIG. 3 is an enlarged perspective view of the surgical drape of FIG. 1 that is folded to form a pocket having two open ends.

Moreover, in one embodiment, referring to FIGS. 1–3, a surgical drape 10 having a certain configuration is illustrated. In particular, the surgical drape 10 includes a base sheet 14 to which a portion of the fabric 12 is attached. For example, in one embodiment, the drape 10 contains a 193-centimeter×305-centimeter base sheet 14 made of polypropylene spunbond and meltblown layers. Moreover, the fabric 12, in one embodiment, has exterior dimensions of 65 centimeters×100 centimeters.

In some embodiments, such as shown in FIG. 1, at least a portion of the fabric 12 is attached to the base sheet 14 using conventional attachment methods, such as thermal, adhesive, or mechanical bonding. In one embodiment, for example, the fabric 12 can be adhesively laminated to the base sheet 14 using an aqueous adhesive, such as an adhesive sold under the name L 8052-01 by Findley Adhesives.

In general, the area of attachment between the fabric 12 and the base sheet 14 can vary. For example, in some embodiments, as shown in FIG. 1, an area less than or equal to the area bounded by the edges 90 and 65 can be bonded to the base sheet 14 using conventional attachment methods.

Figure 8:
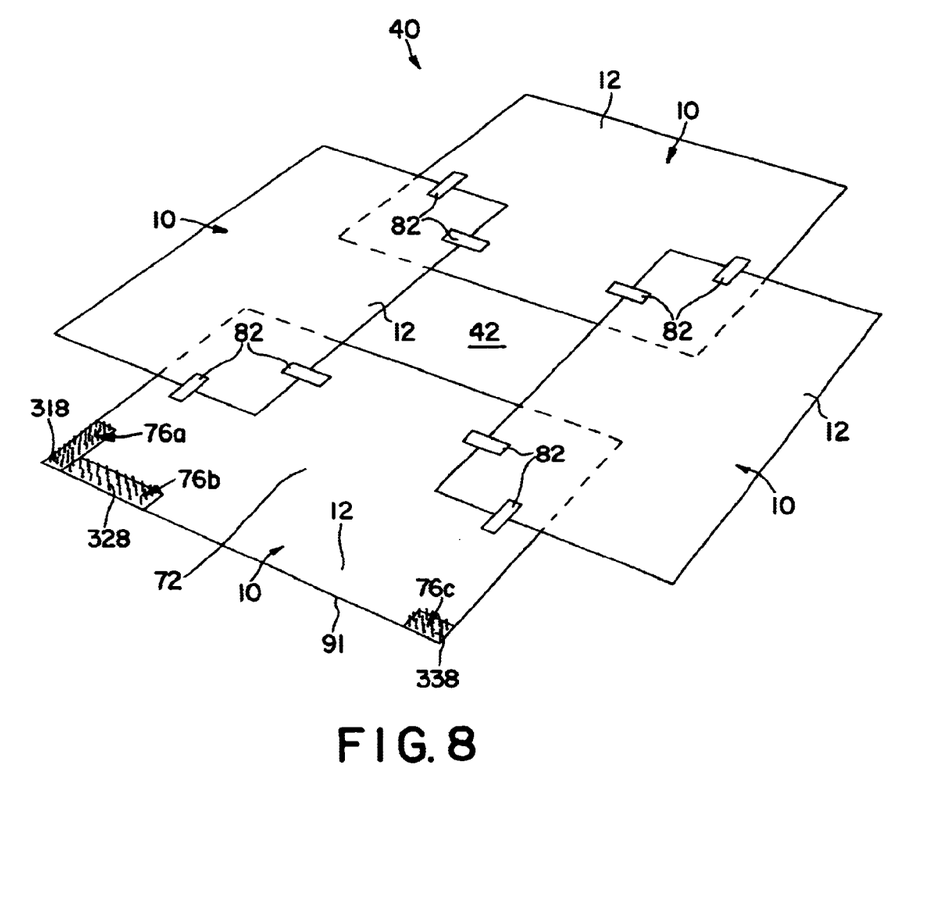
FIG. 8 is a perspective view of a plurality of surgical drapes formed according to another embodiment of the present invention that are connected together via hook fasteners to provide a surgical opening.
Figure 13:
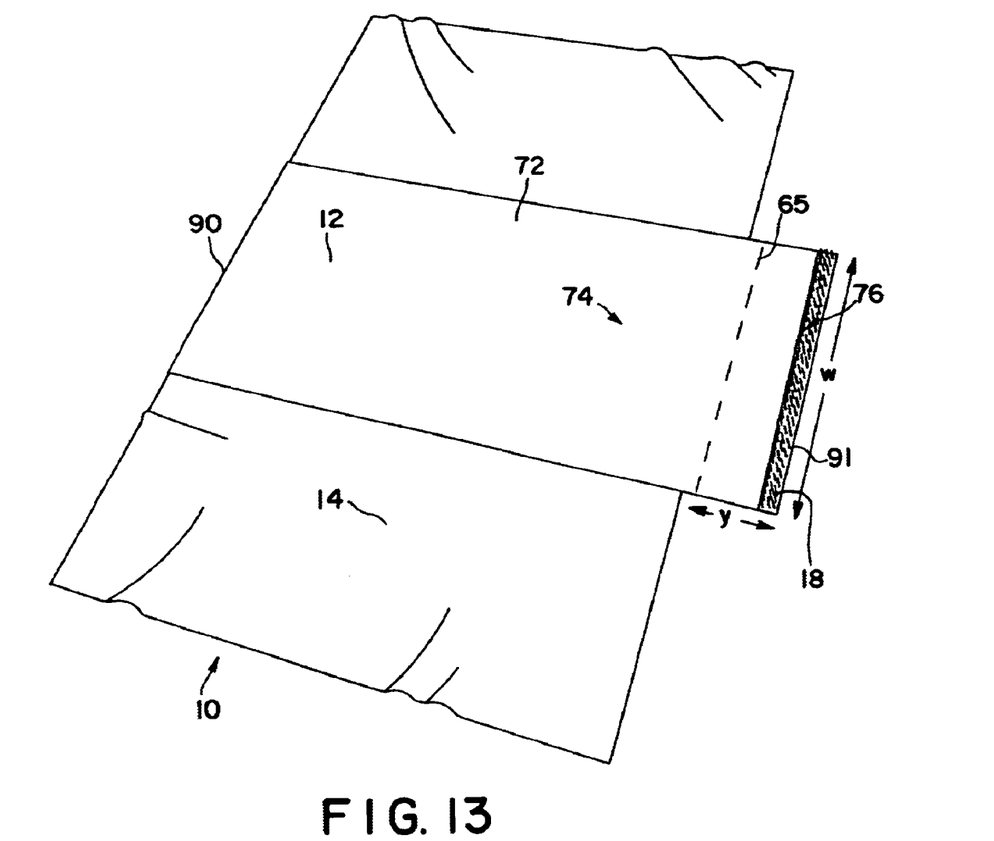
FIG. 13 is a perspective view of another embodiment of a surgical drape of the present invention.

Typically, this attachment area is such that an edge 91 of the fabric 12 does not extend over a fenestration opening 16. However, as shown in FIG. 8, it should be understood that a base sheet 14 is not necessarily required and, if desired, the fabric 12 may form substantially the entire surgical drape 10. Moreover, as shown in FIG. 13, a fenestration opening is not always required.

As stated, in some embodiments, the drape 10 includes a fenestration opening 16 that can be placed over an operating site during surgery. For example, in one embodiment, a 10-centimeter×30.5-centimeter fenestration opening 16 is provided. In the embodiment depicted in FIG. 1, the fabric 12 also surrounds each side of the fenestration opening 16 so that it may absorb fluids therefrom. However, in some embodiments, the fabric 12 can be placed adjacent to only one, two, or three sides of the opening 16.

If desired, the fabric 12 may be constructed so as to have properties that differ from the base sheet 14. For example, large-sized drapes that are intended to completely cover the patient and provide substantial fluid absorption can use a relatively high basis weight, absorbent multilayered nonwoven fabric 12 surrounding the fenestration 16, while the rest of the drape's base sheet 14 can be relatively low in basis weight and include a barrier, such as a film, to inhibit the passage of fluids through the drape. Moreover, as stated above, it should be understood that the surgical drape of the present invention need not contain a separate base sheet 14.

In another embodiment, such as shown in FIG. 8, a drape kit 40 is provided that includes a plurality of surgical drapes 10 each formed from the fabric 12. For example, in one embodiment, the drape kit 40 includes at least one hook fastener 82 for securing at least two drapes 10 together. As specifically shown in FIG. 8, four drapes 10 and eight hook fasteners 82 are provided. Specifically, each drape 10 is secured to two other drapes 10 via two hook fasteners 82. However, it should be understood that the drapes 10 can be attached to each other using other methods as well.

The drape kit 40 may include any number of drapes 10 greater than one, and any number of fasteners 82. As shown, the four drapes 10 are arranged so as to define a fenestration opening 42 between the drapes. Such an opening 42 could be created by medical personnel for performing a surgical technique on a patient without the need for a specifically designed drape. Thus, the drapes 10 of the drape kit 40 could be arranged in any desired manner over the top of a patient and operating table to provide much greater flexibility to the medical personnel. Also, the number of different specific drapes that might need to be purchased and inventoried is reduced through use of the drape kit 40.

Various embodiments of the materials and methods used to construct a surgical drape in accordance with the present invention will now be described in more detail. In general, the fabric 12 may be made from the same or different materials as the base sheet 14. For example, as shown in FIG. 1, the regions 74 and 76 of the fabric 12, as discussed in more detail below, may be constructed from nonwoven layers, adhesive layers, film layers, etc. Moreover, some or all of the fabric 12 may be constructed so as to be hydrophilic or hydrophobic, and may be chemically treated to achieve the desired water absorbency properties. For instance, the fabric 12 and/or one or more layers of the fabric 12 may be treated with a surfactant in a manner such as described in U.S. Pat. No. 5,540,979, which is incorporated herein in its entirety by reference thereto for all purposes.

Figure 6:
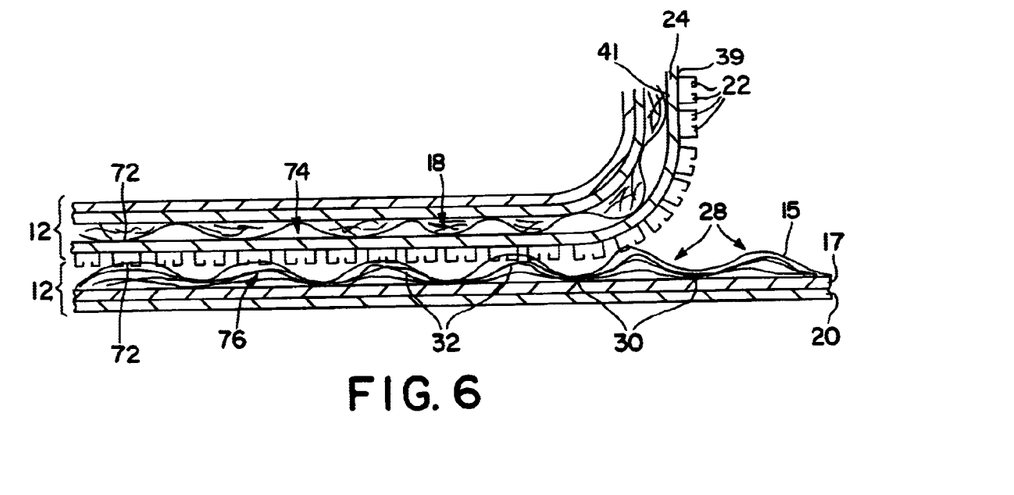
FIG. 6 is a partial sectional view showing the construction of a folded component of a surgical drape formed according to one embodiment of the present invention.
Figure 7:
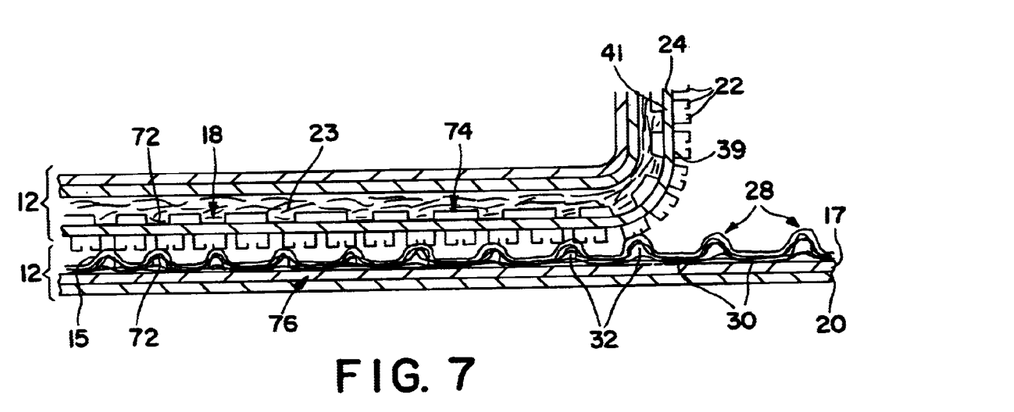
FIG. 7 is a partial sectional view showing the construction of a folded component of a surgical drape formed according to another embodiment of the present invention.

Referring to FIGS. 6–7, in one particular embodiment, the fabric 12 is made from three layers. In particular, FIG. 6 depicts a point bonded fabric, while FIG. 7 depicts a point unbonded fabric, both of which are suitable for use in the present invention in that they provide loops that can releasably engage one or more hooks. For instance, the hooks can be structures adapted for use as a mechanical fastener component and having projections of a profile, height, density, geometry and orientation so as to be capable of releasably attaching to a loop. The projections need not be in the actual form of a hook, but may have other configurations, such as a mushroom shape, for example. Some suitable hook materials contain from about 16 to about 620 hooks per square centimeter and hook heights of from about 0.00254 cm to about 0.19 cm. For example, suitable hooks can be obtained from Velcro International of Manchester, N.H. and 3M Corp. of St. Paul, Minn. Various types of hooks and loops are also described in U.S. Pat. No. 6,055,987 to Griesbach, et al. and U.S. Pat. No. 5,997,981 to McCormack, et al., which are incorporated herein in their entirety by reference thereto for all purposes.

Referring to FIGS. 6–7, for example, the fabric 12 includes a nonwoven layer 15 disposed on one surface of the fabric 12. The nonwoven layer 15 can generally have a variety of basis weights. For example, in one embodiment, the layer 15 has a basis weight of about 64 grams per square meter. In addition, the nonwoven layer 15 can be formed in a variety of ways and can be formed from a variety of different materials. For example, in one embodiment, the nonwoven layer 15 is a spunbonded fabric containing fibers and/or filaments having diameters of about 2.0 denier and made from a copolymer of propylene with 3.5% ethylene (e.g., Union Carbide 6D43 from Union Carbide Corp.) having a basis weight of 20 grams per square meter. Moreover, in this embodiment, the nonwoven layer 15 is bonded by a repeating pattern of discretely fused areas spaced apart to give 111 fused areas per square inch and a 17.7% total bonded area.

In another embodiment, the nonwoven layer 15 is a spunbond fabric formed from two layers of multicomponent fibers and/or filaments, such as described in U.S. Pat. No. 5,418,045, which is incorporated herein in its entirety by reference thereto for all purposes. In particular, the spunbond fabric is bonded so that a plurality of point unbonded circular areas of about 0.4 centimeters are spaced approximately 0.5 centimeters apart in a hexagonal (close packing) arrangement. The upper surface of the spunbonded fabric may be composed of fibers and/or filaments having a diameter of about 9.0 denier (e.g., circular in cross-section and have polymeric components of Exxon 3445 polypropylene and Dow ASPUN 6811A linear low density polyethylene arranged in a side-by-side configuration at 49% by weight with the remainder being titanium dioxide pigment). The lower surface of the spunbonded fabric may be composed of fibers and/or filaments that have a diameter of about 2.0 denier and have the same composition as the 9-denier fibers and/or filaments mentioned above. Moreover, in one embodiment, the spunbonded fabric is bonded by a repeating pattern of discretely fused areas spaced apart to give a total bond area of about 15%.

Although not required, in addition to the nonwoven layer 15, additional layers may also be provided. For example, in the embodiment shown in FIGS. 6–7, two layers 17 and 20 are provided that are secured to the nonwoven layer 15. In some instances, the layers 17 and 20 can impart fluid barrier attributes to the drape 10 and improve moisture vapor permeability. For instance, the layers 17 and 20 can be made from meltblown webs, film materials, and the like.

In one embodiment, the layer 20 is a barrier film made from about 47% by weight linear low density polyethylene (Dowlex NG 3310 available from Dow Chemical Co.), about 48% by weight Supercoat™ (a ground, stearic acid coated calcium carbonate available from English China Clay), and about 5% by weight low density polyethylene (Dow 4012 available from Dow Chemical Co.). In another embodiment, the barrier layer 20 is a film sold under the name Code XXII Blue by Clopay Corporation.

In one embodiment, the barrier film layer 20 is secured to the nonwoven layer 15 by an adhesive layer 17. For example, the adhesive layer 17 can be a meltblown web made from an amorphous polyolefin, such as Rextac 2730, which is sold by Huntsman Corporation and has a basis weight of about 3 grams per square meter. In another embodiment, the adhesive layer 17 is a meltblown web treated is to be hydrophilic and that has a basis weight of about 34 grams per square meter.

A variety of lamination techniques can also generally be utilized to laminate the layers 17 and 20 to the nonwoven layer 15. For example, in one embodiment, the film layer 20 is initially provided with a thickness of between about 0.0010 to about 0.0015 inches. Thereafter, the film is stretched in one direction to four times its original dimension in the stretched direction and then laminated to the spunbond layer 15 by the meltblown adhesive layer 17. The layers can then be laminated using conventional techniques. For example, in one embodiment, the meltblown adhesive layer 17 can be thermally laminated to the spunbond layer 15 using discrete bond points, such as described in U.S. Pat. No. 5,540,979.

Regardless of the materials or methods used in forming the fabric 12, in one embodiment, the nonwoven layer 15 of the fabric 12, as shown in FIGS. 1 and 6–7, has a surface 72 that defines a loop-element region 74 and at least one hook-element region 76. For example, a hook-element region can refer to an area defined by any portion of a surface of a fabric on which one or more hook fasteners are disposed. Moreover, a loop-element region can refer to an area defined by any portion of a surface of a fabric on which a hook fastener is not disposed and on which loops are disposed that are engageable with the hook fastener when the fabric is folded. For instance, the loop-element region may be defined by an area of loops that is continuous or may be defined by various sections of loops separated by one or more other regions.

For example, in one embodiment, as shown in FIGS. 1 and 6–7, the loop-element region 74 is defined by a surface 72 of the nonwoven layer 15 that includes a plurality of strands 28 (e.g., fibers, filaments, etc.) that are arranged to form a plurality of loops 32 extending between bonds 30. Moreover, in the depicted embodiment, the loop-element region 74 includes the entire fabric 12, except for the hook-element region 76.

Further, the hook-element region 76 includes at least one hook fastener 18 disposed on the hook-element region 76. For example, referring again to FIGS. 6–7, the hook fastener 18 has a backing layer 24 having an upper surface 39 and a lower surface 41. The upper surface 39 includes a number of protrusions 22 extending therefrom that are engageable with the loops 32. Although illustrated herein as having a hook-shape, it should be understood that the protrusions 22 can have various other shapes as well. In fact, the size, shape, and density of protrusions 22 can depend on the type of nonwoven layer 15 utilized, etc. It should also be understood that other methods of attaching the hook fastener 18 to the nonwoven layer 15 can also be utilized.

As shown, the lower surface 41 of the backing layer 24 is also attached to the surface 72 of the fabric 12 at the hook-element region 76 and can generally be secured to fabric 12 in a variety of ways. For example, in one embodiment, the backing layer 24 can be integrally formed with the fabric 12 using thermal, adhesive, or mechanical securing methods, such as are well known in the art. In another embodiment, the backing layer 24 can have protrusions on its lower surface 41 that are similar or identical to the protrusions 22 extending from the upper surface 39 as illustrated in FIGS. 6–7 and discussed below. Such protrusions can allow the lower surface 41 of the backing layer 24 to secure to loops contained on the upper surface of the fabric 12.

The type of hook fasteners that can be used include, but are not limited to, strips of Velcro 51-1003 or 51-1004 and XKH-7163A made by 3M. The dimensions of the strips can generally vary depending on the particular placement desired, such as described below. For example, in some embodiments, a hook fastener 18 that is attachable to the fabric 12 can have a length of between about 40 to about 185 centimeters and a width of between about 2.5 to about 7.5 centimeters.

In general, one or more hook-element regions may be utilized such that the hook fastener(s) can be located in a variety of positions. For example, in one embodiment, as shown in FIGS. 1–3, a hook-element region 76 is located adjacent to the edge 91 of the fabric 12 such that one hook fastener 18 is attached at the hook-element region 76 and has a width approximately equal to the width "w" of the fabric 12.

Figure 14:
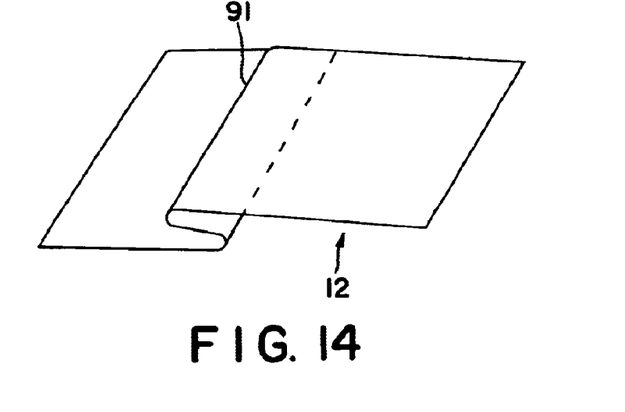
FIG. 14 is a perspective view of another embodiment of a surgical drape of the present invention.

As shown in FIG. 3, an edge 91 of the fabric can be folded such that the region 76 containing the hook fastener 18 is folded in the lengthwise direction (i.e., direction perpendicular to the width "w") of the fabric 12. It should also be understood that the hook-element region 76 can be folded in any given direction, so long as a pocket is capable of forming therefrom. Further, as shown in FIG. 14, it should be understood that the edge 91 need not constitute an end of the fabric 12.

By folding an edge of the fabric 12, such as described above, pockets having a variety of different sizes and configurations can be formed. For example, the hook-element region 76 can be folded in the lengthwise direction of the fabric 12 a certain distance "y" to form a pocket having two open ends. Depending on the pocket size desired, the length "y" of the pocket 100 can generally vary. For example, for drapes that do not have fenestration openings, the length "y" may equal any length less than or equal to the entire length of the fabric. Moreover, for drapes having fenestration openings, it is typically desired that the length "y" does not substantially cover the fenestration opening cut into the fabric. For example, as shown in FIG. 3B, the length "y" of the pocket 100 can be limited such that the end 102 of the pocket remains a certain distance "x" from the fenestration opening 16. For example, in one embodiment, the distance "x" can be about 7.5 centimeters. It should also be understood that certain portions of the hook-element region 76 can be folded in a direction and/or distance different from the other portions of the region 76 to facilitate the formation of pockets that vary in size and shape.

Figure 4:
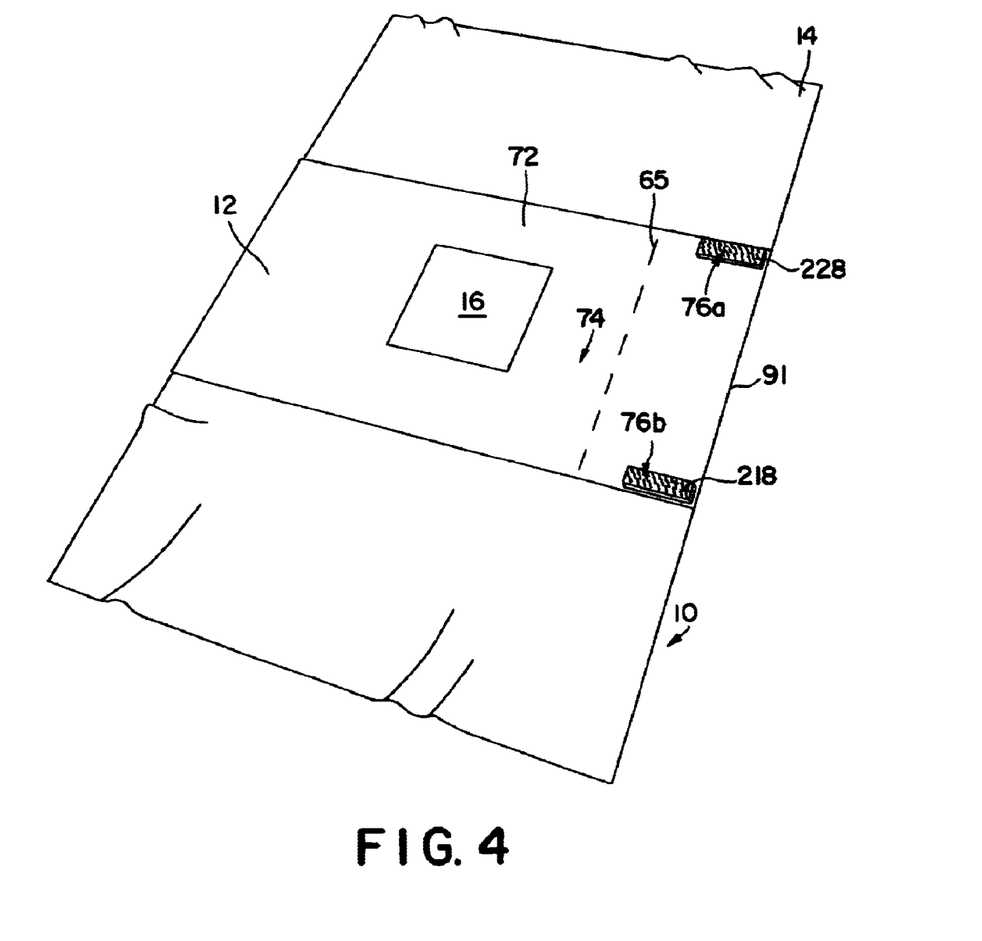
FIG. 4 is a perspective view of another embodiment of a surgical drape of the present invention.
Figure 5:
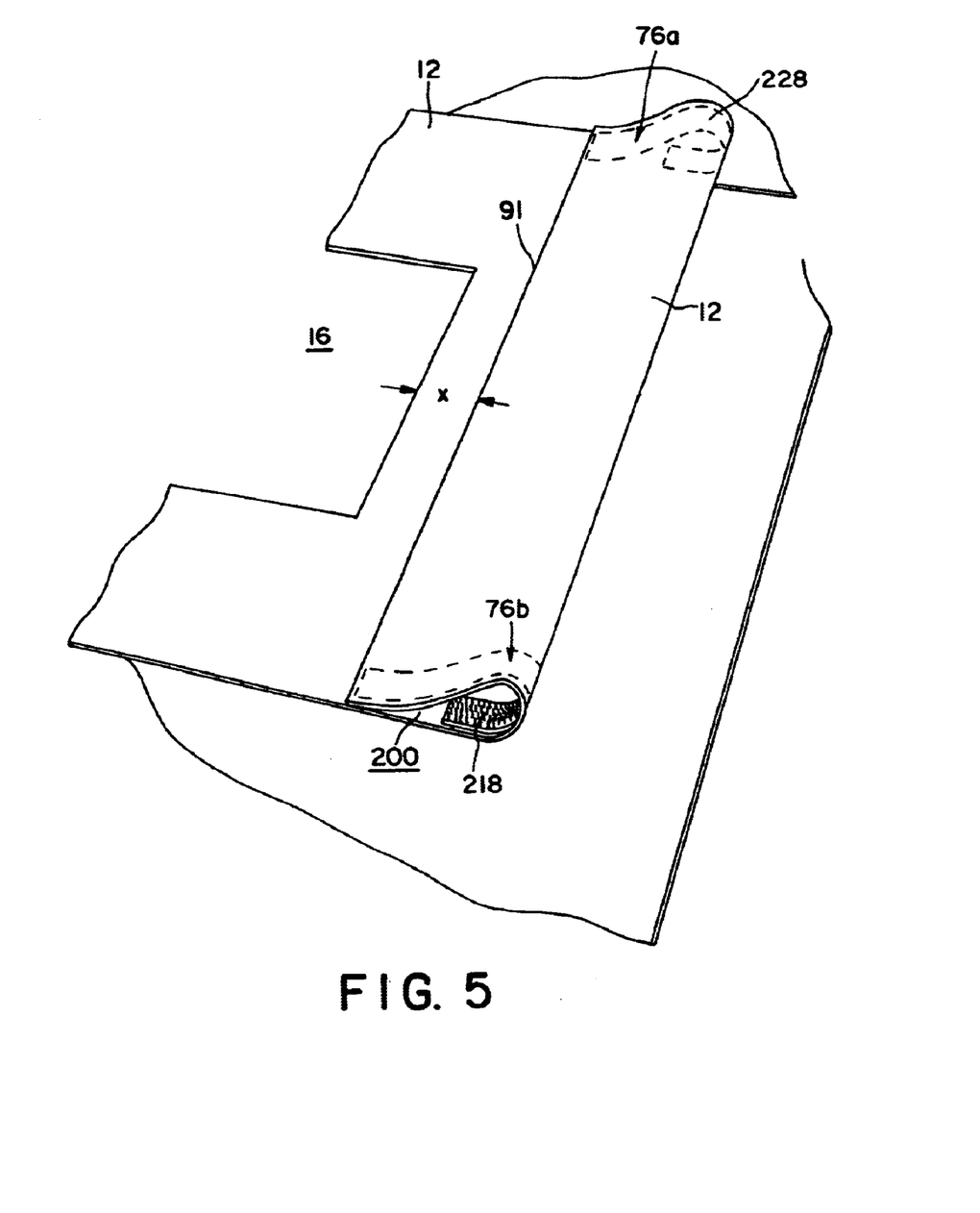
FIG. 5 is an enlarged perspective view of the surgical drape of FIG. 4 that is being folded to form a pocket having two closed ends.

In another embodiment, as shown in FIGS. 4–5, two hook fasteners 218 and 228 are disposed onto hook element regions 76b and 76a, respectively. In this case, when an edge of the fabric is folded, the resulting pocket can have sizes and configurations that may or may not differ from the embodiment discussed above. For instance, as shown in FIG. 5, both hook-element regions 76a and 76b can be folded in the lengthwise direction of the fabric 12 a certain distance "y" to form a pocket 200 having two open ends. In other embodiments, both hook-element regions 76a and 76b can be folded to a greater distance "y" in the lengthwise direction of the fabric 12 to form a pocket having two closed ends. Further, in some instances, the hook-element region 76a can be folded in a different direction and/or distance than the hook-element region 76b to form pockets that differ in size or shape. Moreover, as stated above, in some instances, it may be desired to limit the distance "x" to ensure that the distance "y" is such that it does not completely and/or partially cover a fenestration opening cut into the fabric.

Figure 9:
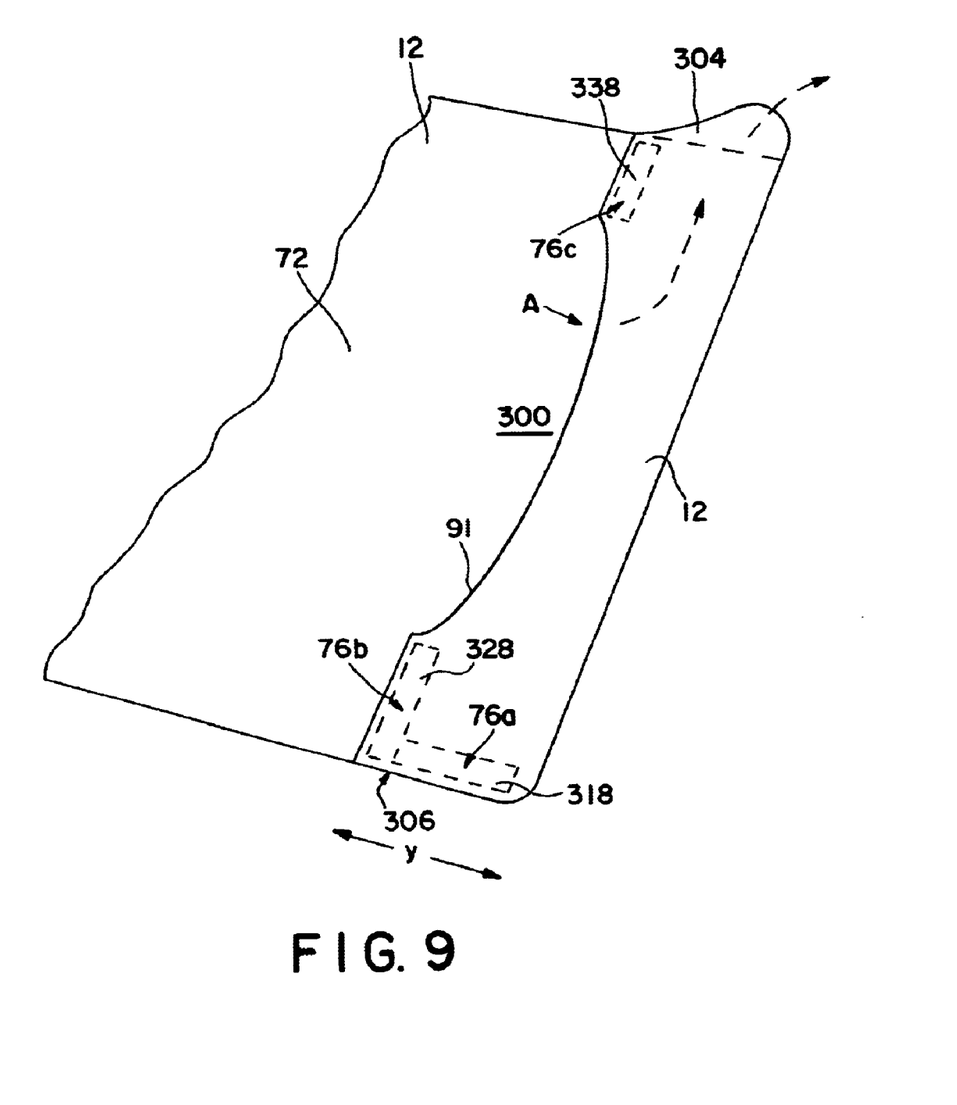
FIG. 9 is an enlarged perspective view of one of the surgical drapes depicted in FIG. 8 that is folded to form a pocket having one open end and one closed end.

Further, in another embodiment, as shown in FIGS. 8–9, three hook fasteners 318, 328, and 338 are disposed onto hook element regions 76a, 76b, and 76c, respectively. In this case, when an edge of the fabric is folded, the resulting pocket can have sizes and configurations that may or may not differ from the embodiments discussed above. For example, as shown in FIG. 9, each hook-element region can be folded in the lengthwise direction of the fabric 12 a certain distance "y" to form a pocket 300 having one open end 304 and one closed end 306. In some instances, such a configuration can enable fluids to enter the pocket 300 and exit through the open end 304 through a path such as shown by the directional arrows A in FIG. 9. Thus, for example, fluids can be more easily drained away from a surgical area when necessary. Moreover, the particular configuration of the pocket 300 having one open end 304 may also enable objects having unconventional shapes or sizes to more easily be secured to the drape. It should also be understood that one or more of the hook-element regions can be folded in a direction and/or distance different from one or more of the other hook-element regions to facilitate the formation of pockets that vary in size and shape.

In some embodiments, as stated above, the hook fasteners can also be formed separate from the fabric. Thus, to secure the edge of the fabric when folded, the hook fasteners can simply be placed in the desired location. For example, in one embodiment, the edge 91 of the fabric can be folded in a manner as depicted in FIG. 5. Thereafter, a separate hook fastener (not shown) can be used to attach the folded edge 91 to the surface 72 of the fabric 12. As shown in FIG. 14, it should also be understood that the edge 91 need not constitute an end of the fabric 12.

Figure 10:
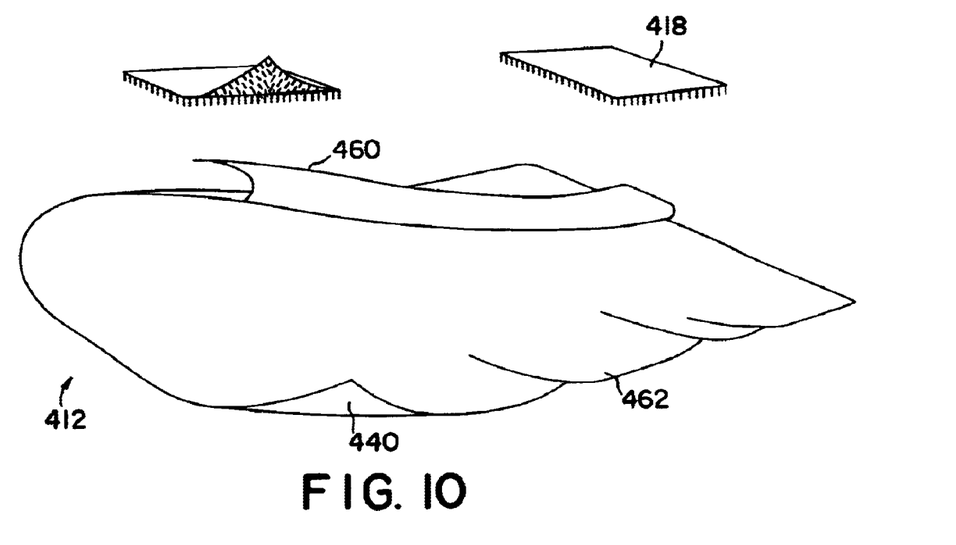
FIG. 10 is a perspective view of a surgical drape formed according to another embodiment of the present invention in which the surgical drape is being double-folded.
Figure 11:
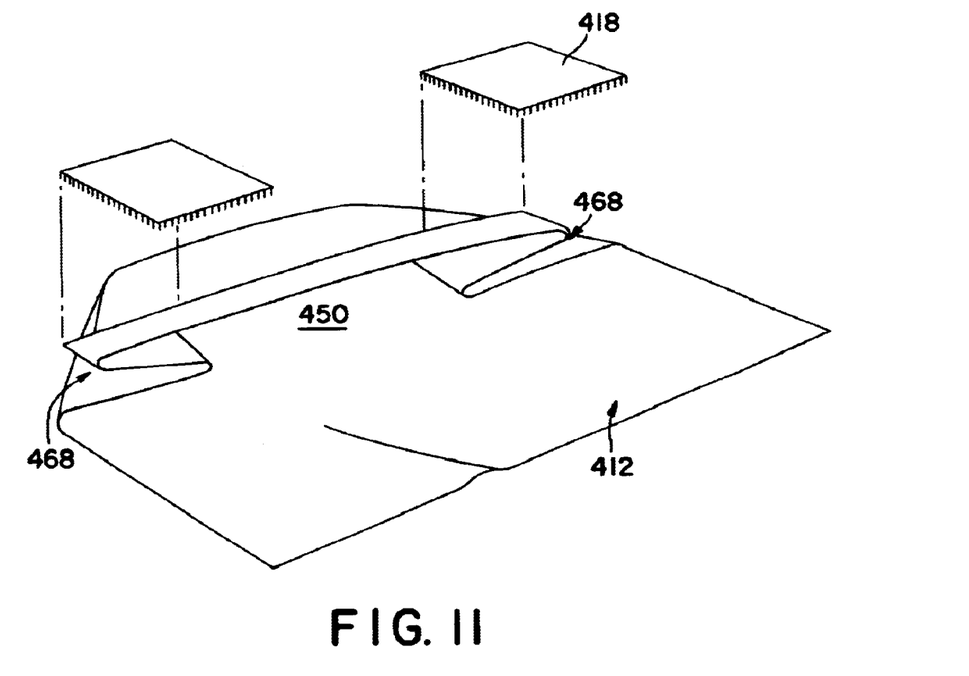
FIG. 11 is a perspective view of the surgical drape of FIG. 10 in which the ends of the fabric edge are being tucked under the double-fold.
Figure 12:
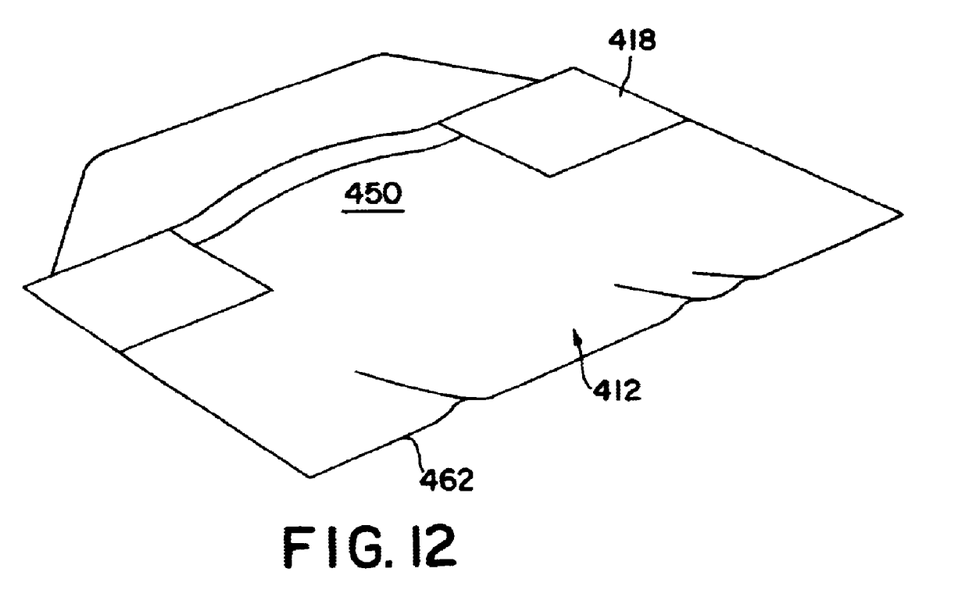
FIG. 12 is a perspective view of the surgical drape of FIG. 10 after being double-folded and tucked.

In general, the placement of the hook fasteners, the number of hook fasteners, and/or the type of fold can be varied to form pockets of different configurations. For example, referring to FIGS. 10–12, another embodiment of the present invention is illustrated that forms a pocket with unattached hook elements. In particular, in this embodiment, a pocket having two closed ends is formed. To form the pocket, an edge of the fabric 412 is first double-folded in a manner depicted in FIG. 10. Specifically, an edge 460 of the fabric 412 is folded in a lengthwise direction towards the opposing edge 462 of the fabric 412 and then folded in an opposite direction. Such a double-fold may be particularly useful when the bottom portion 440 of the fabric 412 is not capable of engaging the hooks of a hook fastener 418, such as when the bottom portion 440 is formed from a film. Once double-folded, the ends 468 of the fold are then tucked under the fold in a manner as depicted in FIG. 11. Thereafter, one or more hook fasteners 418 can then be placed over the fold. As a result, as shown in FIG. 12, a pocket 450 having two closed ends is formed with at least two unattached hook elements. It should also be understood that other fold configurations can be utilized to form pockets having various configurations. For instance, in one embodiment, the edge 460 of the fabric need not be double-folded, particularly when the bottom portion 440 of the fabric 412 contains a loop material. Moreover, similar to the embodiment shown in FIG. 14, it should be understood that the edges 460 and 462 need not constitute an end of the fabric 412.

As a result of the present invention, various objects (e.g., surgical tools) are positionable and repositionable in a variety of ways within a pocket formed on the fabric 12. For example, some surgical tools and their components that can held within a pocket formed according to the present invention include, but are not limited to, fiber optical cords, endoscopic tubing, cords for pencils, smoke evacuator tubing, irrigation/aspiration tubing, and the like. Moreover, a pocket formed according to the present invention can have various other benefits, such as allowing the drainage of fluids away from a surgical site.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of forming a surgical drape with a pocket, said method comprising:
   providing a fabric including a nonwoven layer, the nonwoven layer having a surface including a plurality of strands, the strands being arranged on the surface with a plurality of bonds spaced about the surface and a plurality of loops extending between the bonds;
   forming a pocket by folding an edge of the fabric in a certain direction such that said edge engages a portion of the fabric;
   securing the edge of the fabric to said portion of the fabric using at least one hook-fastener that includes a plurality of hooks, said hooks being engageable with said loops.

2. A method as defined in claim 1, wherein said fabric forms substantially the entire surgical drape.

3. A method as defined in claim 1, wherein said surgical drape further includes a base sheet, said fabric being secured to the base sheet.

4. A method as defined in claim 3, wherein said base sheet defines a surface area and the fabric covers only a portion of the surface area.

5. A method as defined in claim 1, wherein said nonwoven layer includes a spunbond material.

6. A method as defined in claim 1, wherein said nonwoven layer includes a meltblown material.

7. A method as defined in claim 1, wherein said pocket has two open ends.

8. A method as defined in claim 1, wherein said pocket has one open end and one closed end.

9. A method as defined in claim 1, wherein said pocket has two closed ends.

10. A method as defined in claim 1, wherein said at least one hook fastener is formed integral with said fabric.

11. A method as defined in claim 1, wherein said at least one hook fastener is formed separate from said fabric.

12. A method as defined in claim 1, further comprising the step of double-folding said edge.

13. A method as defined in claim 1, further comprising the step of tucking under at least one end of said edge.

14. A method of forming a surgical drape with a pocket, said method comprising:
    providing a fabric having a surface defining a loop-element region and a hook-element region, wherein said loop-element region is defined by a surface of a nonwoven layer that includes a plurality of strands, said strands being arranged on the surface of said nonwoven layer with a plurality of bonds spaced about the surface of said nonwoven layer and a plurality of loops extending between the bonds, said hook-element region having at least one hook fastener integrally disposed thereon, said hook fastener including a plurality of hooks;
    forming a pocket by folding an edge of the fabric in a certain direction such that said edge engages a portion of the fabric;
    securing the edge of the fabric to said portion of the fabric with said at least one hook-fastener.

15. A method as defined in claim 14, wherein said fabric forms substantially the entire surgical drape.

16. A method as defined in claim 14, wherein said surgical drape further includes a base sheet, said fabric being secured to the base sheet.

17. A method as defined in claim 16, wherein said base sheet defines a surface area and the fabric covers only a portion of the surface area.

18. A method as defined in claim 14, wherein said pocket has two open ends.

19. A method as defined in claim 14, wherein said pocket has one open end and one closed end.

20. A method as defined in claim 14, wherein said pocket has two closed ends.

21. A surgical drape comprising:
    a fabric having a surface defining a loop-element region and a hook-element region, wherein said loop-element region is defined by a surface of a nonwoven layer that includes a plurality of strands, said strands being arranged on the surface of said nonwoven layer with a plurality of bonds spaced about the surface of said nonwoven layer and a plurality of loops extending between the bonds, said hook-element region having at least one hook fastener integrally disposed thereon, said hook fastener including a plurality of hooks, wherein at least one edge of said fabric is foldable such that said hooks are engageable with said loops to form a pocket.

22. A surgical drape as defined in claim 21, wherein said fabric forms substantially the entire surgical drape.

23. A surgical drape as defined in claim 21, wherein the surgical drape further includes a base sheet, said fabric being secured to the base sheet.

24. A surgical drape as defined in claim 23, wherein said base sheet defines a surface area and the fabric covers only a portion of the surface area.

25. A surgical drape as defined in claim 21, wherein said nonwoven layer includes a spunbond material.

26. A surgical drape as defined in claim 21, wherein said nonwoven layer includes a meltblown material.

27. A surgical drape as defined in claim 21, wherein said pocket has two open ends.

28. A surgical drape as defined in claim 21, wherein said pocket has one open end and one closed end.

29. A surgical drape as defined in claim 21, wherein the pocket has two closed ends.

* * * * *